United States Patent [19]

Welters et al.

[11] Patent Number: 4,489,057
[45] Date of Patent: Dec. 18, 1984

[54] U.V. ABSORBING COSMETIC COMPOSITIONS

[75] Inventors: Reiner Welters; Juergen Gehlhaus; Gernot Moeschl, all of Darmstadt, Fed. Rep. of Germany

[73] Assignee: Merck Patent Gesellschaft mit beschraenkter Haftung, Darmstadt, Fed. Rep. of Germany

[21] Appl. No.: 148,606

[22] Filed: May 12, 1980

Related U.S. Application Data

[63] Continuation-in-part of Ser. No. 727,806, Sep. 29, 1976, abandoned.

[30] Foreign Application Priority Data

Oct. 3, 1975 [DE] Fed. Rep. of Germany ....... 2544180

[51] Int. Cl.³ .......................... A61K 7/42; A61K 9/12
[52] U.S. Cl. ....................................... 424/47; 424/59; 424/60; 424/168
[58] Field of Search .................... 424/59, 47

[56] References Cited

U.S. PATENT DOCUMENTS

| | | | |
|---|---|---|---|
| 2,807,604 | 9/1957 | Gordon | 260/45.95 R |
| 2,945,002 | 7/1960 | Van Allan | 260/45.95 R |
| 3,001,970 | 9/1961 | Ebel et al. | 260/45.95 R |
| 3,123,647 | 3/1964 | Duennenberger et al. | 568/333 |
| 3,240,752 | 3/1966 | Tamblyn | 260/45.95 R |
| 3,882,142 | 5/1975 | Walworth et al. | 548/373 |

Primary Examiner—Dale R. Ore
Attorney, Agent, or Firm—Millen & White

[57] ABSTRACT

Cosmetic compositions containing dibenzoylmethane compounds of the formula

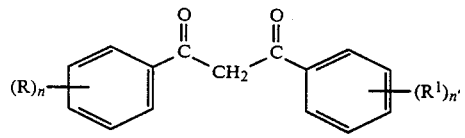

wherein R and R$^1$ are straight-chain or branched alkyl of 1-8 carbon atoms, n an integer from 0-3 and n' an integer from 1-3, dissolved in the fatty components of said composition have superior sun-protection efficiency.

4 Claims, 1 Drawing Figure

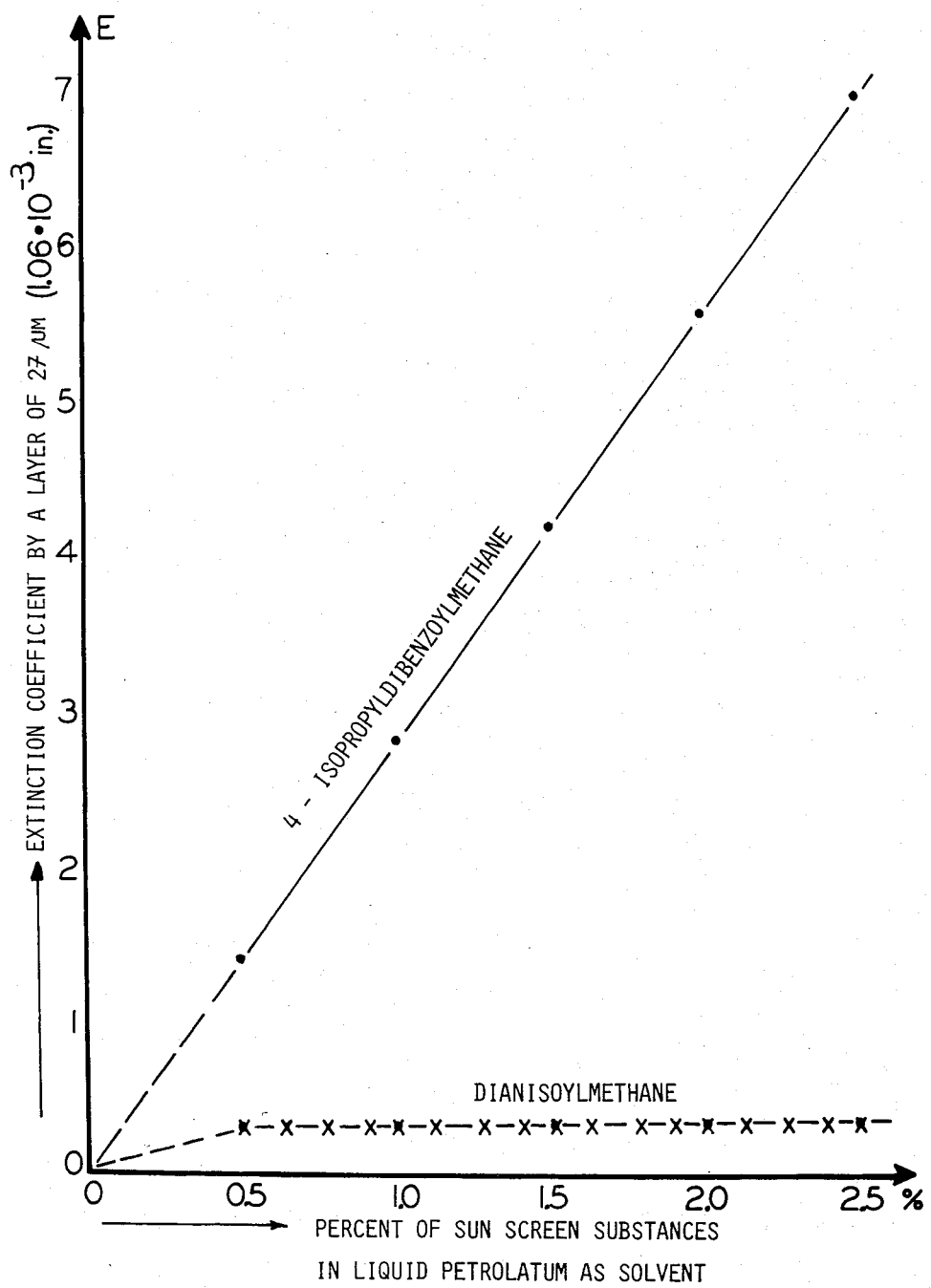

U.V. ABSORBING COSMETIC COMPOSITIONS

CROSS REFERENCE TO RELATED APPLICATIONS

This application is a continuation-in-part of application Ser. No. 727,806, filed Sept. 29, 1976 now abandoned.

BACKGROUND OF THE INVENTION

This invention related to U.V.-absorbing agents suitable for cosmetic purposes.

U.V.-rays from sunlight have long-lasting action on the human skin. Rays of the 280 to 230 nm wavelength range cause sunburn or erythema, especially in fair-skinned persons. Even "browning" rays of 320 to 400 nm (U.V.-A), wavelength range, often regarded as desirable, can have permanently undesirable effects on the condition and appearance of the skin. These include pathological changes in the skin, e.g., light dermatoses. Especially in the case of long-term action, U.V.-A rays also cause more rapid aging of the skin exposed to light, especially facial skin, than of skin protected by clothing. Effective agents for protection against rays in the 280 to 320 nm (U.V.-B) range are known. See German Patent Specification No. 2,051,824, now U.S. Pat. No. 3,781,417.

Dianisoylmethane, which has been used as U.V. filter, absorbs U.V. rays up to about 380 nm. However, in the region below 330 nm, dianisoylmethane has limited absorption and, furthermore, is only sparingly soluble in conventional cosmetic oils and fats. Methoxy- and hydroxy-substituted benzophenones, also used as "broad band filters", have a very low fat solubility and exhibit satisfactory absorption behavior only up to about 340 nm.

The hydroxy-ketones of U.S. Pat. No. 3,123,647 also show a very low fat and oil solubility and do therefore not fulfill the requirements for a sun-protection agent for cosmetics. It has been found out that the U.V. absorbance of a certain U.V. absorbing compound physically measured in the usual way using a very low concentrated solution of the compound in a suitable solvent does not in all cases correlate with the sun-protection factor of a cosmetic composition containing this compound. Surprisingly it has been found that U.V. absorbing compounds which are not fully soluble in cosmetic compositions show less satisfactory sun-protection factors than is to be expected from the physically measured absorbance in solution.

With other words, the physically measured absorbance of a certain compound does not give any hint whether this compound will be an effective U.V. absorbing agent when it is incorporated in a cosmetic formulation. The completely different behavior of an absorbing compound in a cosmetic carrier compared with the physically measured absorption in low concentration in a solvent not suitable for cosmetics can be shown by the following experiment:

Dianisoylmethane, a structurally close sun-protection agent used in compositions of the art, shows a comparable good U.V. absorption like the compounds of this invention when measured in the normal way using a concentration of some mg/100 ml and a path length of 10 mm. However, using a path length of only about 20 $\mu$m, which is realistic for the application on human skin, and a concentration of some g/100 ml in a typical cosmetic carrier the situation is completely different.

In FIG. 1 the extinction coefficients of dianisoylmethane and 4-isopropyldibenzoylmethane are plotted against the concentration in liquid paraffine. It is clearly shown that in the case of 4-isopropyldibenzoymethane there is a linear dependency of the extinction coefficient from the concentration. That means, that with rising concentrations very high sun-protection factors can be reached.

In the case of dianisoylmethane from the physically measured absorbance in low concentration about the same extinction as for 4-isopropyldibenzoylmethane should be expected. However, as FIG. 1 shows, on the one hand the extinction coefficients are much lower than expected and on the other hand there is no linear dependency from the concentration but already at low concentrations a plateau is reached. This means, that in the case of dianisoylmethane it is not possible to reach higher sun-protection factors by raising the concentration of the active compound in the formulation. This completely unsatisfactory result was reached although the compound was micronized and homogeneously distributed by ultrasonic treatment.

With only partly soluble U.V. absorbing compounds still other serious problems arise, for instance to achieve a homogeneous distribution of the compound in the composition and on the human skin. "Broad band filters" with good solubility and additionally good U.V. absorption which are suitable for the use in cosmetics have hitherto not been known.

Numerous U.V. stabilizers for polymers are known. However, these U.V. stabilizers as a rule are not suitable for cosmetic purposes since the requirements for a U.V. stabilizer in polymers are completely different from those of a U.V absorbing agent in cosmetics. To be used in cosmetics a compound must at least fulfill the following requirements: good U.V. absorption, good chemical stability, photostability, as little odor as possible, non-staining, tasteless, toxicologically unobjectionable, good toleration by skin and mucous membranes, i.e. non-irritant, non-sensitizing, non-allergenic, easily to be processed, good solubility in the solvents or bases usual for cosmetics, good compatibility with the usual bases, good stability of the finished product.

For a compound to be used in polymers most of these requirements are negligable, other requirements which do not play any role in cosmetics becoming more important, like for instance the ability to stop chain reactions in the polymer.

In practice this means that there are completely divided fields of the art; on the one hand the polymer specialist knowing all about the physical and chemical behavior of polymers; and on the other hand the specialist dealing with the complex and still widely unknown physiological and biochemical behavior and reactions of living tissue, the human skin.

Thus, although there are numerous U.V. absorbing agents already known, there is a continuing need for agents to protect human skin against the effects of harmful U.V. rays. Such agents should, in a suitable medium, contain an active material which absorbs the rays of 285 to 380 nm as completely as possible, is non-toxic and compatible with the skin, has good solubility in cosmetic oils and, especially, has high light stability.

SUMMARY OF THE INVENTION

In a compositional aspect, this invention relates to a U.V. radiation absorbing cosmetic composition containing an effective concentration of at least one U.V. absorbing compound of Formula I

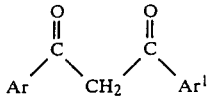
(I)

wherein Ar is

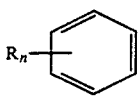

and Ar¹ is

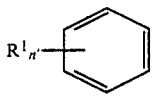

and R and R¹ each are alkyl of 1–8 carbon atoms, n is an integer from 0–3 and n' and integer from 1–3, wherein said U.V. absorbing compound is dissolved in the fatty components of a cosmetically acceptable oil, emulsion, cream, ointment or aerosol carrier adapted for application to human skin.

In a method-of-use aspect, this invention relates to a method for the protection of human skin against an overdoes of U.V. radiation in the region between 285 and 380 nm which comprises coating the skin exposed to sunlight with the foregoing U.V. radiation absorbing cosmetic composition.

In a process aspect, this invention relates to a process for the preparation of U.V. radiation absorbing cosmetic compositions which comprises the incorporation of at least one compound of Formula I in a cosmetically acceptable fat, oil or wax and intermixing the thus obtained solution with appropriate components to form a cosmetically acceptable oil, emulsion, cream, ointment or aerosol composition adapted for application to human skin.

This invention also includes fat-containing cosmetic compositions, which contain at least one compound of Formula I.

DETAILED DESCRIPTION

Preparation of 2-, 3- and 4-methyldibenzoylmethane is described in Chemische Berichte 86, 1263 (1953), preparation of symmetrical ditoluylmethanes in J. Amer. Chem. Soc. 81, 4682 (1959) and J. Org. Chem. 36, 1447 (1971). 2,4,6-trimethyldibenzoylmethane and 2,2',4,4',6,6-hexamethyldibenzoylmethane are described in Zeitschrift für anorg. und analyt. Chem. 340, 319 (1965).

Compounds of Formula I can also be present in the form of tautomers of Formula Ia:

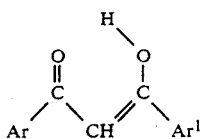
(Ia)

An equilibrium between the two forms in many cases is substantially towards compounds of Formula Ia. In the specification and claims, references to compounds of Formula I therefore include compounds of Formula Ia.

Compounds of Formula I can be substituted on one or both phenyl nuclei. However, those substituted on only one nucleus are preferred.

If n or n' is 1, R or R¹ is preferably in the 2- or 4-position. However, it has been found out, surprisingly, that if n equals zero and R¹ is in the 4-position at least an alkyl with 2 carbon atoms is needed to obtain compounds with an outstanding good solubility in fats and oils for cosmetics. Thus, although 4-methyl-dibenzoylmethane is still suitable it is not preferred among compounds of Formula I. Preferred are compounds with one or two alkyl groups of 1–4 carbon atoms, which in the case of two alkyl groups can be combined on one phenyl nucleus, preferably in the 2,4-position, or on both phenyl nuclei, preferably in the 4,4'-position. Substitution in the 3-position and, e.g., 2,5- or 3,5-positions is also possible. These compounds are also within the scope of the invention.

When both phenyl nuclei are substituted, substitution on both nuclei can be the same but this need not be the case. Dibenzoylmethanes having different substituents on both phenyl nuclei can be prepared without difficulty.

R and R¹ include alkyl of 1–8 carbon atoms, e.g., methyl, ethyl, propyl, isopropyl, n-butyl, isobutyl, sec.-butyl, t.-butyl, n-pentyl, isopentyl, neopentyl, hexyl, heptyl and octyl, including isomers of the higher alkyl substituents.

Of compounds of Formula I, those which are most preferred are:
2-methyldibenzoylmethane
4-isopropyldibenzoylmethane
4-tert.-butyldibenzoylmethane
2,4-dimethyldibenzoylmethane
4,4'-diisopropyldibenzoylmethane.

Alkyl-substituted dibenzoylmethanes of Formula I are outstandingly suitable active materials for absorption of U.V.-A- and U.V.-B-rays since they absorb rays with a wavelength of 285 to 380 nm almost completely in low concentration, possess very good light stability, and are very readily soluble in the conventional solvents for cosmetics, especially in fat-containing compositions.

Compound of Formula I have good to excellent solubility in cosmetic oils and fats. 4-methyldibenzoylmethane is about three times as soluble in paraffin oil as unsubstituted dibenzoylmethane and 4-isopropyldibenzoylmethane is almost completely miscible therewith.

High stability to alkalis of compounds of Formula I, in comparison with unsubstituted dibenzoylmethane, is also surprising. Therefore, alkaline cosmetic formulations made therefrom are also very stable to storage.

The very good light stability of compounds of the invention is also remarkable. In a xenon test, only a very slight increase of transmissivity was observed after 24 hours of irradiation.

The high fat and oil solubility of compounds of Formula I is especially advantageous in the preparation of compositions containing comparatively high concentrations of the active compounds. Although the absorptivity of the active compounds is very high, comparatively high concentrations of the agents can be appropriate in compositions intended for very sensitive skin or which are to be used in regions having very intensive solar radiation.

Some compounds of Formula I are known but all of them can be prepared by known methods.

Bromine can be added to a benzylideneacetophenone, obtainable by condensation of a substituted benzaldehyde with a substituted acetophenone, substituted by identical or different alkyl on one or both phenyl rings. Reaction of a resultant dibromide with a base, e.g., sodium methylate or ethylate, gives a corresponding substituted dibenzoylmethane.

Asymmetrically or symmetrically substituted dibenzoylmethanes can be prepared by reaction of a substituted acetophenone with a substituted benzoic acid ester, using a strong base, e.g., sodamide.

Symmetrically substituted dibenzoylmethanes can also be prepared by reaction of an arylcarboxylic acid vinyl ester with aluminium chloride under Friedel-Crafts conditions. See J. Org. Chem., Vol. 36, 1447 (1971).

Compounds of Formula I can be formulated with salve or cream bases to provide fatty or non-fatty light protective salves or skin creams or, by mixing with solvents, possibly adding emulsifiers, liquid light-protection or skin-care preparations.

Suitable solvents include, for example: hydrocarbons, e.g., solid or liquid paraffin, crystal oil, ceresin, ozokerite and montan wax; vegetable or animal oils, fats and waxes, e.g., olive oil, mineral oil or carnauba wax, lanolin and spermaceti; fatty acids and esters thereof, e.g., stearic acid, palmitic acid, oleic acid, glycerol mono- or distearate, glycerol monooleate, isopropyl myristate, isopropyl stearate, and butyl stearate; and alcohols, e.g., ethyl, isopropyl, cetyl, stearyl, palmityl, and hexyldodecyl alcohol. Polyhydroxy alcohols, e.g., glycol, glycerol, and sorbitol, which simultaneously serve as moisturizing agents, can also be used.

Other suitable materials are, e.g., emulsifiers for oil-in-water and water-in-oil systems, such as commercially available ionic, non-ionic, cationic or anionic active or ampholytic emulsifiers. Thickening agents, e.g., methyl, ethyl, or carboxymethyl cellulose; polyacrylic acid; tragcaanth, agar agar, and gelatin can also be added. As needed or as desired, additional materials, e.g., perfumes, preservatives and/or physiologically compatible coloring materials, can be added.

Preferred cosmetically acceptable carriers are those based on a hydrocarbon or vegetable or animal oil, fat or wax.

The compositions of the invention can contain one or more additional U.V. absorbers, e.g., p-methylbenzylidene-D,L-camphor or its sulfonic acid Na salt, 2-phenylbenzimidazole-5-sulfonic acid sodium salt, 3,4-dimethylphenylglyoxylic acid sodium salt, 4-phenylbenzophenone, 4-phenylbenzophenone-2'-carboxylic acid isooctyl ester, p-methoxycinnamic acid esters, 2-phenyl-5-methylbenzoxazole, and p-dimethylaminobenzoic acid esters.

Compounds of Formula I are used in compositions of the invention in a U.V. absorbing effective amount. The exact concentration is not critical and depends substantially on the intended use. Generally, compositions of the invention contain 0.5–15% by weight of compounds of Formula I. Compositions are preferred which contain 0.5–8.0% by weight of compounds of Formula I. If the compositions contain additional U.V. absorbers, the total amount of U.V.-absorbing compounds usually varies between 0.5 and 15% by weight, preferably between 0.5 and 10%.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius;, unless otherwise indicated, all parts and percentages are by weight.

PREPARATION OF THE ACTIVE MATERIALS

EXAMPLE A

Into a solution of 55.4 g of p-toluylideneacetophenone in 250 ml of chloroform is added dropwise at 5° to 10° 40 g of bromine. The crystals which precipitate out towards the end of the reaction are filtered with suction, washed with methanol and dried. The thus-obtained 87.5 g of 1-benzoyl-2-p-tolyl-1,2-dibromoethane, m.p. 168°, is added in portions to 180 ml of methanolic sodium methylate solution, containing 2 moles of methylate per mole of bromo compound. After two hours under reflux, HCl is added and the mixture heated under reflux for 5 minutes. Water is added thereto. Upon cooling, 35 g of 4-methyldibenzoylmethane crystallize out, m.p. 84° C.

EXAMPLE B

To a suspension of 29.7 g of sodamide in 400 ml of toluene is added dropwise first 61.5 g of isopropylacetophenone and then 51.7 g of benzoic acid methyl ester. The mixture is stirred overnight at room temperature. After the addition of water and acidification, the organic phase is separated. Solvent is removed and the product distilled. The oil which distills over is recrystallized from methanol to obtain 54 g of 4-isopropyldibenzoylmethane, m.p. 46°.

EXAMPLE C

A suspension of 39 g of sodamide in 540 ml of toluene is mixed with 88 g of 4-tert.-butylacetophenone and subsequently with 87 g benzoic acid methyl ester, and left overnight with stirring. After acidification, the organic phase is separated and washed. Solvent is removed and the residue distilled. The oil which distills over is recrystallized to obtain 80 g of 4-tert.-butyldibenzoylmethane, m.p. 97°.

EXAMPLE D

Analogously to Example C, starting from 2-methylacetophenone and benzoic acid methyl ester, 2-methyldibenzoylmethane, b.p. 157°/0.04 mmHg, is obtained.

EXAMPLE E

Analogously to Example C, starting from 4-methylacetophenone and benzoic acid methyl ester, 4-methyldibenzoylmethane, m.p. 84°, is obtained.

EXAMPLE F

Analogously to Example C, starting from 4-isopropylacetophenone and 4-isopropylbenzoic acid methyl ester, 4,4'-diisopropyldibenzoylmethane, m.p. 48°, is obtained.

EXAMPLE G

Analogously to Example C, starting from 4-n-octylacetophenone and benzoic acid methyl ester, 4-n-octyldibenzoylmethane, b.p. 232°-240°/0.15 mmHg, is obtained.

EXAMPLE H

Analogously to Example C, starting from 2,4-dimethylacetophenone and benzoic acid methyl ester, 2,4-dimethyldibenzoylmethane, m.p. 62°, is obtained.

EXAMPLE I

Analogously to Example C, starting from 2,5-dimethylacetophenone and benzoic acid methyl ester, 2,5-dimethyldibenzoylmethane, b.p. 182°/0.01 mmHg, is obtained.

Examples of Skin Protective Agents:

EXAMPLE 1

Skin Protection Oil

| | |
|---|---|
| 4-isopropyldibenzoylmethane | 4 g |
| isopropyl myristate | 15 g |
| paraffin liquid | to 100 g |
| perfume | as desired |

The isopropyldibenzoylmethane is dissolved in the oil base with gentle stirring.

EXAMPLE 2

Skin Protection Gel

| | |
|---|---|
| 4-isopropyldibenzoylmethane | 4 g |
| paraffin liquid | 19 g |
| $C_{18}$-$C_{12}$ saturated fatty acid triglycerides | 15 g |
| isopropyl myristate | 5 g |
| pyridoxol tris-(palmitic acid ester) | 0.1 g |
| Vaseline white | to 100 g |
| perfume | as desired |

4-Isopropyldibenzoylmethane and pyridoxol tris-palmitate are dissolved, with stirring, in the fatty components. Perfume is added subsequently.

EXAMPLE 3

Skin Protection Foam (oil/water emulsion)

| | | |
|---|---|---|
| (1) | 4-isopropyldibenzoylmethane | 4 g |
| | isopropyl myristate | 10 g |
| | 2-octyldodecanol | 5 g |
| | stearic acid | 3.5 g |
| | cetyl alcohol ethoxylate | 8.5 g |
| (2) | 4-hydroxybenzoic acid methyl ester | 0.1 g |
| | water | to 100.0 g |
| | perfume | as desired |

4-Isopropyldibenzoylmethane is dissolved in the melted fat heated to 75°. Then is stirred into the aqueous phase (2) at the same temperature. Perfume is added at about 40°.

EXAMPLE 4

Skin Protection Cream (water/oil)

| | |
|---|---|
| 4-isopropyldibenzoylmethane | 4 g |
| spermaceti | 3 g |
| glycerol monostearate | 2 g |
| 4-hydroxybenzoic acid propyl ester | 0.25 g |
| Vaseline with emulsifying lanolin alcohols | 42 g |
| 4-hydroxybenzoic acid propyl ester Na salt | 0.25 g |
| water | to 100 g |
| perfume | as desired |

EXAMPLE 5

Skin Protection Milk (oil/water)

| | | |
|---|---|---|
| (1) | 4-isopropyldibenzoylmethane | 4 g |
| | paraffin liquid | 15 g |
| | $C_8$-$C_{12}$ saturated fatty acid triglycerides | 5 g |
| | isopropyl myristate | 3 g |
| | cetyl alcohol | 2.5 g |
| | sorbitan monostearate | 1.8 g |
| | polyoxyethylene sorbitan monostearate | 2.7 g |
| (2) | 4-hydroxybenzoic acid methyl ester | 0.2 g |
| | Karion F liquid (sorbitol solution (70%)) | 3 g |
| | water | to 100 g |
| | perfume | as desired |

4-Isopropyldibenzoylmethane is dissolved in the fat phase (1) heated to 75°. This is mixed with the hot aqueous phase, also at 75°. Subsequently, it is perfumed and homogenized.

EXAMPLE 6

Skin Protection Cream (oil/water)

| | | |
|---|---|---|
| (a) | 4-isopropyldibenzoylmethane | 16 g |
| | ceresin wax | 5 g |
| | $C_8$-$C_{12}$ saturated fatty acid triglycerides | 10 g |
| | cetyl alcohol | 1.5 g |
| | emulsifier mixture with stearyl and cetyl alcohol and their ethylene oxide addition products | 8 g |
| | 4-hydroxybenzoic acid propyl ester | 0.1 g |
| (b) | glycerol | 1.5 g |
| | Propane-1,2-diol | 1.5 g |
| | sorbitol solution (70%) | 4 g |
| | 4-hydroxybenzoic acid propyl ester sodium salt | 0.15 g |
| | water | to 100 g |
| (c) | perfume | |

The aqueous phase (b), heated to about 75° C., is stirred into the melted fat phase (a), at the same temperature. It is perfumed at about 40° C. and subsequently homogenized.

EXAMPLE 7

Skin Protection Cream (oil/water)

| (a) 4,4'-diisoproyldibenzoylmethane | 8 g |
|---|---|
| ceresin wax | 5 g |
| C$_8$–C$_{12}$ saturated fatty acid triglycerides | 10 g |
| cetyl alcohol | 1.5 g |
| emulsifier mixture with stearyl and cetyl alcohol and their ethylene oxide addition products | 8 g |
| 4-hydroxybenzoic acid propyl ester | 0.1 g |
| (b) aqueous phase as in Example 6 | |
| (c) perfume as desired | |

The method of preparation is the same as that of Example 6.

EXAMPLE 8

Skin Protection Cream (water/oil)

| (a) 4,4'-diisopropyldibenzoylmethane | 8 g |
|---|---|
| cetyl alcohol | 1.5 g |
| beeswax | 1.5 g |
| paraffin, liquid | 3 g |
| cholesterol | 1 g |
| C$_8$–C$_{12}$ saturated fatty acid triglycerides | 8 g |
| mixture of glycerol and sorbitan fatty acid esters, wax-containing | 9 g |
| ceresin | 5 g |
| glycerol and sorbitan fatty acid esters partially ethoxylated | 6 g |
| spermaceti | 2 g |
| 4-hydroxybenzoic acid propyl ester | 0.1 g |
| (b) aqueous phase as in Example 6 | |
| (c) perfume as desired | |

This method of preparation is as in Example 6.

EXAMPLE 9

Skin Protection Cream (oil/water)

| (a) 2,5-dimethyldibenzoylmethane | 12 g |
|---|---|
| cetyl alcohol | 1.5 g |
| C$_8$–C$_{12}$ saturated fatty acid triglycerides | 10 g |
| ceresin | 5 g |
| emulsifier mixture with stearyl and cetyl alcohol and their ethylene oxide addition products | 8 g |
| 4-hydroxybenzoic acid propyl ester | 0.1 g |
| (b) aqueous phase as in Example 6 | |
| (c) perfume as desired | |

The method of preparation is as in Example 6.

EXAMPLE 10

Skin Protection Cream (water/oil)

| (a) 2,5-dimethyldibenzoylmethane | 10 g |
|---|---|
| C$_8$–C$_{12}$ saturated fatty acid triglycerides | 5 g |
| spermaceti | 3 g |
| glycerol monostearate | 3 g |
| Vaseline with emulsifying lanolin alcohols | 37 g |
| 4-hydroxybenzoic acid proyl ester | 0.1 g |
| (b) aqueous phase as in Example 6 | |
| (c) perfume as desired | |

The method of preparation is as in Example 6.

EXAMPLE 11

Skin Protection Lotion (oil/water)

| (a) 2-methyldibenzoylmethane | 8 g |
|---|---|
| cetyl alcohol | 2.5 g |
| paraffin, liquid | 5 g |
| C$_8$–C$_{12}$ saturated fatty acid triglycerides | 6 g |
| ceresin | 5 g |
| sorbitan monostearate | 1.8 g |
| polyoxyethylene sorbitan monostearate | 2.7 g |
| 4-hydroxybenzoic acid propyl ester | 0.1 g |
| (b) aqueous phase as in Example 6 | |
| (c) perfume as desired | |

The method of preparation is as in Example 6.

EXAMPLE 12

Skin Protection Cream (water/oil)

| (a) 2-methyldibenzoylmethane | 6 g |
|---|---|
| spermaceti | 3 g |
| glycerol monostearate | 2 g |
| Vaseline with emulsifying lanolin alcohols | 40 g |
| 4-hydroxybenzoic acid propyl ester | 0.1 g |
| (b) aqueous phase as in Example 6 | |
| (c) perfume as desired | |

The method of preparation is as in Example 6.

EXAMPLE 13

Skin Protection Cream (oil/water)

| (a) 2,4-dimethyldibenzoylmethane | 6 g |
|---|---|
| Vaseline | 10 g |
| isopropyl myristate | 10 g |
| stearyl and cetyl alcohol, sulfated up to about 10% | 15 g |
| 4-hydroxybenzoic acid propyl ester | 0.1 g |
| (b) aqueous phase as in Example 6 | |
| (c) perfume as desired | |

The method of preparation is as in Example 6.

EXAMPLE 14

Skin Protection Cream (oil/water)

| (a) 4-tert.-butyldibenzoylmethane | 2 g |
|---|---|
| C$_8$–C$_{12}$ saturated fatty acid triglycerides | 6 g |
| ceresin | 4 g |
| Vaseline | 4 g |
| isopropyl myristate | 4 g |
| stearyl and cetyl alcohol, sulfated up to about 10% | 15 g |
| 4-hydroxybenzoic acid propyl ester | 0.1 g |
| (b) aqueous phase as in Example 6 | |
| (c) perfume as desired | |

The method of preparation is as in Example 6.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A cosmetic composition containing a U.V. absorbing effective concentration of 4-isopropyldibenzoylmethane dissolved in the fatty components of a cosmetically acceptable oil, emulsion, cream, ointment or aerosol carrier adapted for application to human skin.

2. The composition of claim 1, containing 0.5–8.0% by weight of 4-isopropyldibenzoylmethane.

3. The composition of claim 1, wherein the cosmetically acceptable carrier is based on a hydrocarbon or vegetable or animal oil, fat or wax.

4. A method for the protection of human skin against an overdose of U.V. radiation in the region between 285 and 380 nm which comprises coating the skin exposed to sunlight with a composition according to claim 1.

* * * * *